United States Patent [19]

Kakiuchi et al.

[11] 4,245,495
[45] Jan. 20, 1981

[54] NEEDLE-TYPE COLLOID OSMOMETER

[75] Inventors: Yoshihiro Kakiuchi; Takashi Arai, both of Sapporo, Japan

[73] Assignee: Hokkaido University, Sapporo, Japan

[21] Appl. No.: 943,258

[22] Filed: Sep. 15, 1978

[30] Foreign Application Priority Data

Dec. 27, 1977 [JP] Japan .............................. 52-159883

[51] Int. Cl.² .......................................... G01N 13/04
[52] U.S. Cl. ................................................. 73/643
[58] Field of Search .................................... 73/64.3

[56] References Cited
U.S. PATENT DOCUMENTS 3,195,346  7/1965  Ehrmantraut et al. ............... 73/64.3

Primary Examiner—Gerald Goldberg
Assistant Examiner—Joseph W. Roskos
Attorney, Agent, or Firm—Ladas & Parry

[57] ABSTRACT

A needle-type colloid osmometer is disclosed. This osmometer comprises a hollow needle body having at least one hole at its outer wall and acting as a part of a pressure sensing chamber, a cylindrical semipermeable membrane fitting the needle body therein, and a sampling chamber receiving the needle body with the membrane. The osmometer is usable for measuring colloid osmotic pressure of blood, lymph, body fluid or the like in the fields of clinical pathology, physiology, biochemistry, biology and the like.

4 Claims, 9 Drawing Figures

NEEDLE-TYPE COLLOID OSMOMETER

This invention relates to a needle-type colloid osmometer for measuring a colloid osmotic pressure of blood, lymph, body fluid or the like which is used in biological examination and the like.

When a solution composed of a solvent and a solute is contacted with a solvent containing no solute through a semipermeable membrane, the solvent penetrates through the membrane into the solution and reaches its equilibrium state with time. For instance, a vessel 11 is divided into two chambers 13a, 13b by a semipermeable membrane 12 as shown in FIG. 1. When these chambers 13a, 13b are filled with a solution and a solvent, respectively, the solvent penetrates through the semipermeable membrane 12 into the solution as shown by arrows in FIG. 1. Finally, when the equilibrium state is produced between the chambers 13a and 13b, a level of pressure in the chamber 13a is higher than that in the chamber 13b owing to the movement of the solvent. Such a difference of pressure is an osmotic pressure h. The value of the osmotic pressure is proportional to the concentration of the solution.

This theory has been established in 1886 by Dutch physicist, Vant Hoff on a basis of the fact that an osmotic pressure of a sugar solution is quantified in 1874 by German botanist, Pfeffer. According to this theory, the osmotic pressure P is calculated from a product of the gas constant R, an absolute temperature T and a molar concentration C of a solute (i.e., $P=RTC$). As a means for measuring the osmotic pressure, there are known an osmometer using a combination of a semipermeable membrane and a manometer according to the above theory, and an osmometer using a molar depression of freezing point.

Body fluids such as blood plasma, lymph and the like are colloidal solutions containing inorganic salts as well as proteins and the like. A cell membrane of most organisms has a semipermeability which passes water and inorganic salts but does not pass high molecular weight proteins (colloid). The movement of water between blood and tissues is dependent upon a balance of pressure difference between a hydrostatic pressure and a colloid osmotic pressure in the blood plasma and the tissue fluid. In general, it is said that the rupture of such a balance causes symptoms such as edema, dehydration and the like. That is, since the pressure level of the blood is higher than that of the tissue due to the pumping action of a heart, the blood has a force pushing water to the tissue. On the other hand, the colloid concentration of the blood is higher than that of the tissue fluid, so that the blood has also a force absorbing water from the tissue due to the osmotic pressure. As a result, the water content of the tissue fluid is held at a normal state by the balance between both the above forces. Therefore, the measurement of the blood osmotic pressure is very important in physiology and clinical pathology.

In order to measure the colloid osmotic pressure of blood plasma, osmometers using the molar depression of freezing point have been mainly used until a colloid osmometer using a combination of a semipermeable membrane and an electrical manometer has been developed in 1961 by Hansen, and are widely used even at present.

The osmometer using the molar depression of freezing point has such an advantage that the substances including from low molecular weight inorganic salts to high molecular weight proteins can be measured irrespective of the molecular weight of the solute. However, such osmometers determine a very slight molar depression of freezing point ($-1.858°$ C. per 1 mole), so that the reading value is usually limited to 2 mOSM (1 mOSM/kg$\simeq$1 mole/1,000). While, the normal value of human blood plasma is 290 mOSM and only 1.78 mOSM of which is due to the colloid. That is, the colloid osmotic pressure influencing the movement of water in vivo does not come up to only 1% of the total osmotic pressure of the plasma. Therefore, it is very difficult to follow a delicate change of the colloid osmotic pressure by the above molar depression.

The osmometer designed by Hansen (hereinafter referred to as Hansen osmometer) has a structure as shown in FIG. 2 wherein an ultrafilter (sieve membrane) with a molecular weight retentivity of 10,000 (including most colloidal proteins) is used as a semipermeable membrane and a pressure sensing chamber is filled with a physiological saline solution (0.9% NaCl) as a standard.

Referring to FIG. 2, reference numeral 14 is a pressure sensing chamber, the inside of which is filled with the saline solution. The upper opening of the pressure sensing chamber 14 is sealed by an ultrafilter 15. The ultrafilter 15 consists of a semipermeable membrane 15a and a supporting paper 15b superimposed thereunder and is fixed through a clamping body 17 by means of bolt and nut 16. Above the ultrafilter 15 is formed a sampling chamber 18 provided with passages 19a, 19b, through which a blood to be tested is flowed. A pressure inside the pressure sensing chamber 14 is detected by an electrical manometer 21 as a strain of its diaphragm 20.

When a sample such as a blood inclusive of colloid or the like is supplied to the sampling chamber 18, water (including inorganic salts) in the pressure sensing chamber 14 moves into the sampling chamber 18 through the semipermeable membrane 15a due to the osmotic pressure. As a result, the pressure inside the pressure sensing chamber 14 reduces only by the amount of water moved and reaches an equilibrium state when the water movement stops at a point equal to the osmotic pressure. At this time, the osmotic pressure is directly read by the electrical manometer 21. For instance, the manometer 21 used to have a reading accuracy of about 0.5 mmHg.

It is known that 1 mOSM is theoretically equal to 17 mmHg. From this fact, it can be seen that the measuring limit of the molar depression method as mentioned above is 34 mmHg (2 mOSM). On the other hand, the Hansen osmometer has a reading accuracy of at least 30 times higher than that of the osmometer using the molar depression as to the measurement of the colloid osmotic pressure in ideal state.

In the molar depression method, cooling and temperature measuring are made for a spot sample in a vial, so that the continuous measurement is principally impossible. While, the Hansen osmometer using the semipermeable membrane makes it possible to continuously measure and record the colloid osmotic pressure because the sample is continuously flowed through the sampling chamber 18 from the passage 19a to 19b. Thus, the Hansen osmometer can continuously record the osmotic pressure of the blood passing through the blood path every moment, so that it gives a principally favorable merit in this field.

However, the Hansen osmometer cannot provide reproducibility and reliability enough to put into practical use. The great cause results from the structure of this osmometer, particularly the semipermeable membrane composed of a disk type ultrafilter. That is, since the semipermeable membrane is disk type (or sheet type), there are caused delicate and unavoidable troubles in the installing to the pressure sensing chamber 14. In order that this type of the osmometer holds the practically usable performance, at least the following five requirements must be satisfied in the structures of the semipermeable membrane and the pressure sensing chamber and the installing therebetween:

(1) There is no pressure leakage between the pressure sensing chamber and the semipermeable membrane. (If the pressure leakage is caused, an inaccuracy of the measured value becomes large.)

(2) The semipermeable membrane must be always held under a tension so as not to cause a bending under an influence of a pressure change in the pressure sensing chamber. (If the bending is caused, the inaccuracy of the measured value becomes large and the response time is prolonged.)

(3) The effective area of the semipermeable membrane is made large as far as possible in order to promote the rapidity of equilibrium reaction.

(4) There is no air bubble in the pressure sensing chamber and the semipermeable membrane. (Since the bubbles have a large compressibility, a long time is required until pressure equilibrium. In this case, the equilibrium reaction becomes extremely prolonged and also sensitive to temperature change, so that it is difficult to effect an exact measurement.)

(5) The replacement of the semipermeable membrane can be easily performed.

In order to install the disk type semipermeable membrane to the pressure sensing chamber, there is adopted a mechanical fastening means. In this case, however, a high precision mechanical work is required in the manufacture of the pressure sensing chamber supporting the semipermeable membrane and of its contact surface for satisfying the above mentioned requirements. Further, the semipermeable membrane itself is formed by depositing a thin filtering film on the filtering paper base, so that it is fairly poor in the mechanical properties and is liable to be destroyed. Therefore, even if there is provided a good finished pressure sensing chamber, the performances as the osmometer are influenced by the assembling technique of the osmometer, so that a chance satisfying the above requirements is very little. In fact, it has been found from the experience that the chance is less than 5%. As a result, there is no guarantee for success of the biological experiment even by the renewal when replacement of the semipermeable membrane is inevitable during the experiment. That is, the biological experiment often comes to nothing in each replacement of the semipermeable membrane. Accordingly, the Hansen osmometer is not suitable for practical use so far as the semipermeable membrane is a disk type membrane though it is superior in principle.

It is, therefore, an object of the invention to provide a new type of a colloid osmometer utilizing the effect of the semipermeable membrane and satisfying the aforementioned requirements, in which the membrane and the like are easily exchangeable and the continuous measurement can easily be performed.

According to the invention, there is provided a new needle-type colloid osmometer comprising a hollow needle body constituting at least a part of a pressure sensing chamber filled with a standard solution and having at least one hole at its outer wall, a cylindrical semipermeable membrane fitting said needle body therein so as to seal at least said hole, and a sampling chamber receiving said needle body with said membrane and filled with a sample.

The invention will now be described in greater detail with reference to the accompanying drawings, wherein.

Figure 1:
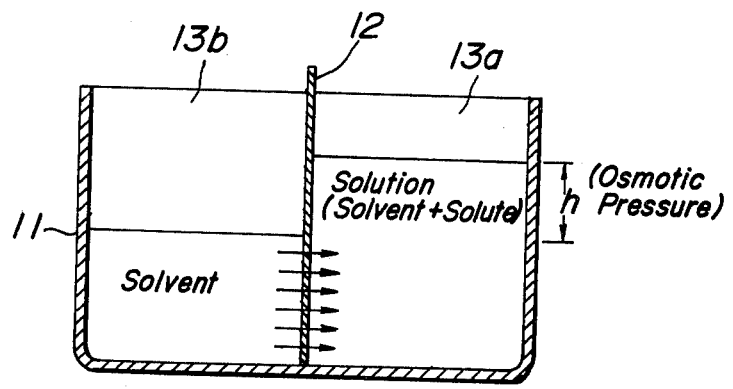
FIG. 1 is a schematical view illustrating the theory of osmotic pressure.
Figure 2:
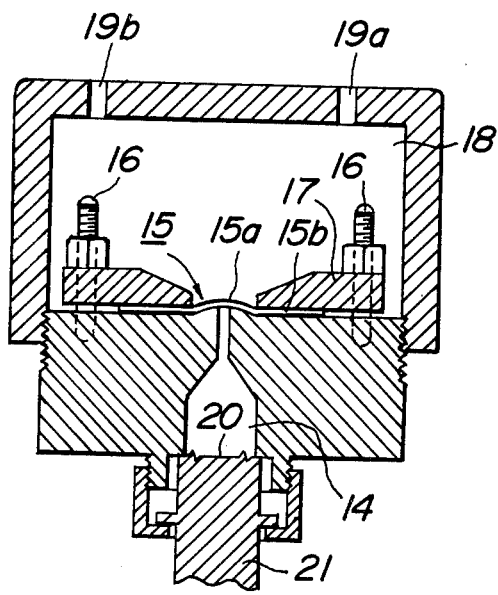
FIG. 2 is a diagrammatically sectional view of the Hansen osmometer usually used as mentioned above.
Figure 3:
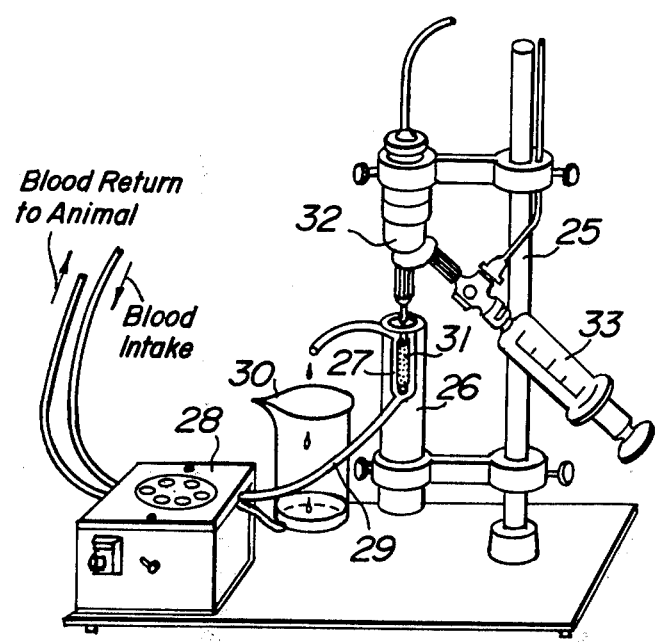
FIG. 3 is a perspective view of a system for the measurement of colloid osmotic pressure using the needle-type colloid osmometer according to the invention.

In FIG. 3 is shown an embodiment of the needle-type colloid osmometer according to the invention for measuring the colloid osmotic pressure of an animal blood. A base 26 including a sampling chamber 27 therein is mounted on a stand 25. In the sampling chamber 27 is supplied a blood withdrawn from an animal to be tested through a pipe 29 by means of a pump 28 at a constant flow rate (usually 4 ml/min). The blood passing through the sampling chamber 27 is received in a beaker 30.

In the sampling chamber 27 is inserted a sensing probe 31 with a semipermeable membrane from top. The sensing probe 31 is connected to an electrical manometer 32. Further, the inside of the sensing probe 31 is filled with a physiological saline solution as a standard by means of a syringe 33.

Figure 4:
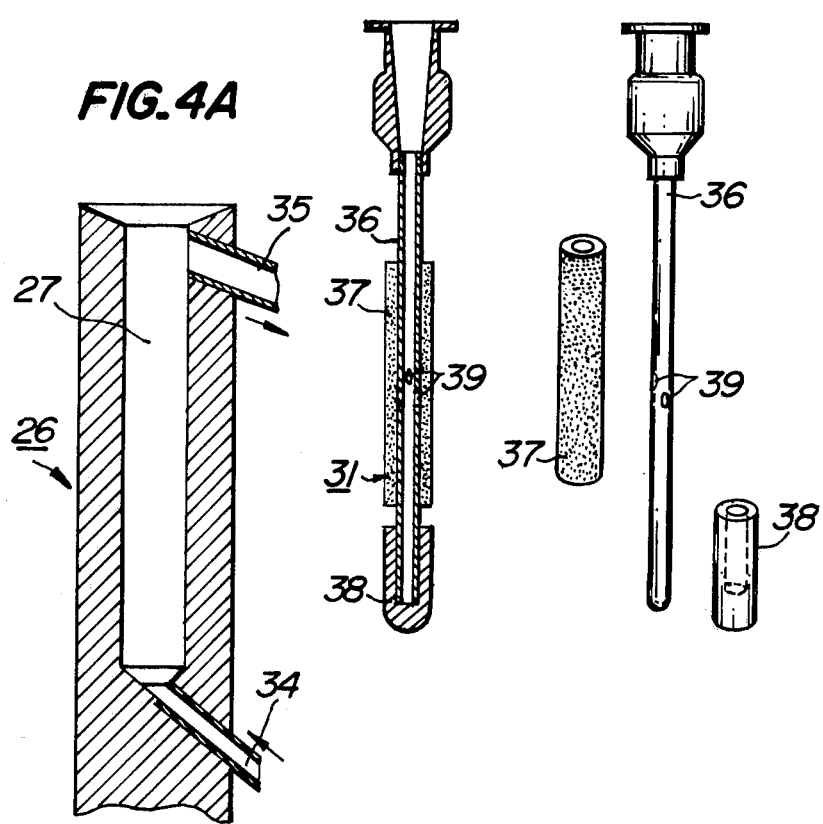
FIGS. 4A to 4C are illustrations of components constituting the needle-type colloid osmometer according to the invention, respectively.

As shown in FIG. 4A, the sampling chamber 27 is formed as an elongate recess with a top opening in the base 26 made of a plastic resin. In order to avoid slow response due to a long washout time of the sample, the sampling chamber 27 has, for example, an inner diameter of 2.5 mm and a length of 40 mm. At the bottom of the sampling chamber 27 is formed an inlet 34 connected to the pipe 29 for the sample and at the top part of the chamber 27 is formed an outlet 35. Therefore, the blood as a sample can be continuously supplied to the sampling chamber 27 by letting to flow the sample from the inlet 34 and overflow it from the outlet 35. Moreover, the sample is exposed to atmosphere at the top opening of the sampling chamber. This has a great advantage of maintaining a steady hydraulic pressure in the sample in the sampling chamber. In the case of spot samples, a small syringe may be connected to the inlet 34 instead of the pipe 29.

FIG. 4B shows the sensing probe 31 with the semipermeable membrane constituting the pressure sensing chamber. The sensing probe 31 consists mainly of a hollow needle body 36 and a cylindrical semipermeable membrane 37. As shown in FIG. 4C, the needle body 36 is, for example, an injection needle (e.g., 21 gauge stainless steel hypodermic needle). The tip opening of the needle is sealed with a tip plug 38 made of silicone rubber or the like. Further, a plurality of holes 39 is drilled in the outer wall of the needle body 36.

By way of an example, the needle body 36 has an outer diameter of 0.83 mm and a length of 33 mm and the each hole 39 has a diameter of about 0.4 mm. The outer surface of the needle body 36 is covered with the cylindrical semipermeable membrane 37 so as to seal the holes 39. For this end, the membrane 37 has an outer diameter of about 1.4 mm and an inner diameter of 0.8 mm which is slightly smaller than the outer diameter of the needle body 36.

The cylindrical semipermeable membrane 37 used herein is a tubular ultrafilter of a hollow fiber made of polyacrylonitrile copolymer having a molecular weight retentivity of 13,000 (C5P, made by Asahi Chemical Industry Co., Ltd.). This tubular ultrafilter possesses active filtering surfaces on both inner and outer walls between which numerous channels are distributed.

In order to read the osmotic pressure detected by the sensing probe 31, any type of electrical blood pressure transducer with a dome is used as the manometer 32 and connected to the sensing probe 31. For instance, a combination of an arterial blood pressure transducer (P23ID, made by Statham Instruments Inc.) and a carrier amplifier (RP-5, made by Nihon Kohden Kabushiki Kaisha) is used as an electrical manometer system.

According to the invention, the needle-type colloid osmometer of the above mentioned structure satisfies easily and surely all of the aforementioned requirements necessary for the combination of the semipermeable membrane with the pressure sensing chamber.

Regarding the requirement (1), by inserting the hollow needle body 36 in the cylindrical semipermeable membrane 37, the pressure leakage of the pressure sensing chamber can be effectively prevented. Particularly, by making the inner diameter of the membrane 37 slightly smaller than the outer diameter of the needle body 36, the effect of preventing the pressure leakage can be surely developed.

Regarding the requirement (2), the semipermeable membrane 37 is subjected to be stretched in the circumferential direction, so that the bending of the membrane becomes fairly less as compared with the case of using the conventional disk type sheet membrane. Further, regarding the requirement (3), by increasing the number of holes formed in the needle body 36 acting as the pressure sensing chamber, the effective area of the semipermeable membrane can easily be increased. Moreover, regarding the requirements (4) and (5), the needle body 36 and the semipermeable membrane 37 are united together to form a part of the pressure sensing chamber, so that the replacement of the membrane can be conducted only by demounting the needle body 36. And also, the removal of air bubbles can be simply and surely conducted together with the replacement of the membrane by removing the tip plug 38 without requiring a great amount of skill.

Figure 5:
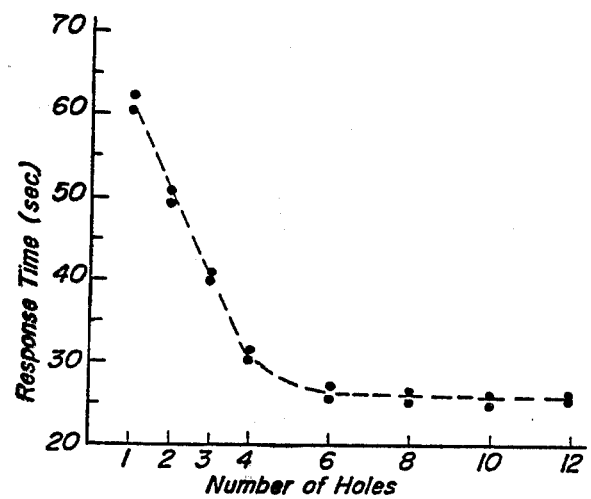
FIG. 5 is a graph showing the relation between the response time of the needle-type colloid osmometer and the number of holes drilled in the outer wall of the needle body.

Moreover, the number of holes 39 drilled in the outer wall of the needle body 36 is one of major factors influencing the response time in the needle-type colloid osmometer according to the present invention because it determines the effective area of the semipermeable membrane for osmosis regarding the requirement (3). FIG. 5 shows the relation between the response time of the osmometer and the number of holes drilled in the needle body. In this case, 14 needle bodies with one to twelve holes were tested in a sample (5% bovine albumin solution) flowing at a flow rate of 4 ml/min in the sampling chamber. As seen from FIG. 5, the response time shortens in proportion to the number of holes between one and four holes, although no remarkable change is observed when there are more than six holes. According to the invention, the number of holes is preferably within a range of 4 to 6.

The needle-type colloid osmometer according to the invention is compared with the conventional Hansen (disk type) osmometer with respect to the performances to obtain a result as shown in the following Table 1.

TABLE 1

| Semipermeable membrane | Diaflo UM-10 made by Amicon | C5P made by Asahi Chemical Industry Co., Ltd. |
|---|---|---|
| Sample | 1% bovine albumin solution | 1% bovine albumin solution |
| Flow rate of sample | 3.5 ml/min | 3.5 ml/min |
| Response time | 80 sec | 40 sec |
| Measured osmotic pressure | 1.67 mmHg | 2.8 mmHg |
| Degree of fidelity $(= \frac{\text{Measured value}}{\text{Theoretical value}} \times 100)$ | 57% | 96% |
| Rate of success | 1/35 | 1/1 |

The comparative experiment of Table 1 was carried out by using a pressure transducer (LPU-0.5-290-III, made by Nihon Kohden Kabushiki Kaisha), an amplifier (RP-5, made by Nihon Kohan Kabushiki Kaisha) and a multichannel pen recorder (KB-88H, made by Rikadenki Kabushiki Kaisha). The supply of the sample was carried out by instantaneously replacing the flowing saline solution (standard) with the sample.

In Table 1, the theoretical value for calculating the degree of fidelity is 2.90 mmHg. Further, the rate of success is expressed by the ratio of numbers obtaining a practical data by repeatedly trying the assembling of the osmometer and replacing the semipermeable membrane. The criterion of the practical data is based on the following conditions:

(a) The error of the measured value is within 10% when the same sample is continuously measured three times;

(b) The response time is within 90 seconds; and (c) The degree of fidelity is not less than 50%.

Figure 6A:
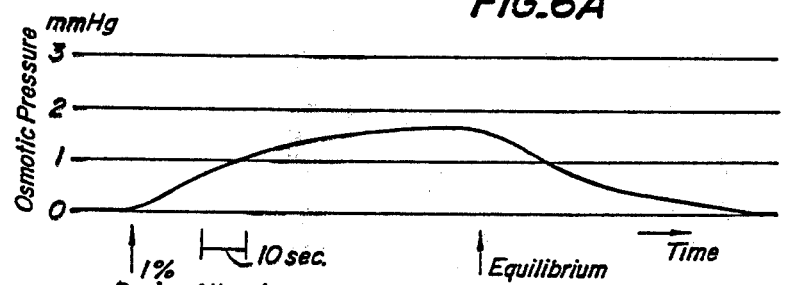
FIGS. 6A and 6B are graphs showing a comparison in performances of the Hansen osmometer and the needle-type colloid osmometer according to the invention.
Figure 6B:
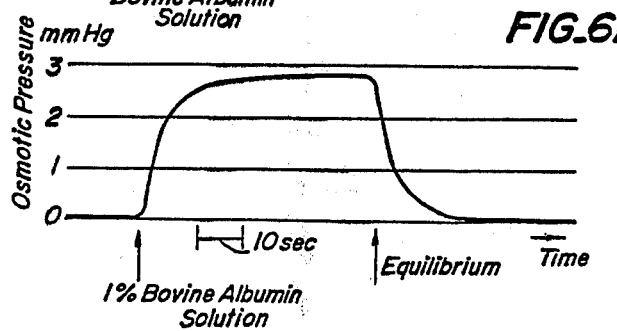

The results of the above comparative experiment is shown in FIG. 6 wherein the performance of the Hansen osmometer is shown in FIG. 6A and that of the needle-type colloid osmometer according to the invention is shown in FIG. 6B. As shown in FIG. 6, the osmometer according to the invention is very good in the responsibility and exhibits a measured value close to the theoretical value of 2.90 mmHg.

According to the invention, the replacement of the semipermeable membrane and the like can be conducted simply and surely, so that the measurement of blood osmotic pressure can easily be performed. Particularly, when a great number of the cylindrical semipermeable membranes are provided, they can be replaced or washed at any time, so that the biological experiment and the like can be easily performed and also the reliability of the measured value becomes higher. Furthermore, the electrical manometer system usually used in the study rooms, laboratories and the like can easily be adopted as a measuring equipment as it is. Moreover the sampling chamber and the sensing probe can be separated with each other, so that the osmometer according to the invention is applicable to any one of flow-through type and spot sample type experiments promptly. In any case, the osmometer according to the invention has satisfactory reproducibility and reliability.

What is claimed is:

1. A needle-type colloid osmometer comprising a hollow needle body constituting at least a part of a pressure sensing chamber filled with a standard solution and having at least one hole at its outer wall, a cylindrical semipermeable membrane fitting said needle body therein so as to seal at least said hole, and a sampling chamber receiving said needle body with said membrane and filled with a sample.

2. A needle-type colloid osmometer as claimed in claim 1, wherein the inner diameter of said cylindrical semipermeable membrane is slightly smaller than the outer diameter of said hollow needle body.

3. A needle-type colloid osmometer as claimed in claim 1, wherein said hollow needle body is an injection needle with a tip opening and is sealed as its tip opening with a detachable plug.

4. A needle-type colloid osmometer as claimed in claim 1, wherein said hollow needle body has 4 to 6 holes at its outer wall.

* * * * *